US00PP11765P2

(12) United States Plant Patent
Trees

(10) Patent No.: US PP11,765 P2
(45) Date of Patent: Feb. 6, 2001

(54) GERANIUM PLANT NAMED 'BALGALSOFI'

(75) Inventor: Scott C. Trees, Nipomo, CA (US)

(73) Assignee: Ball Floraplant, a division of Ball Horticultural Co., West Chicago, IL (US)

( * ) Notice: Under 35 U.S.C. 154(b), the term of this patent shall be extended for 0 days.

(21) Appl. No.: 09/257,100

(22) Filed: Feb. 22, 1999

(51) Int. Cl.[7] ..... A01H 5/00

(52) U.S. Cl. ..... Plt./324
(58) Field of Search ..... Plt./324

*Primary Examiner*—Bruce R. Campell
*Assistant Examiner*—Wendy A Baker
(74) *Attorney, Agent, or Firm*—C. A. Whealy

(57) ABSTRACT

A new and distinct cultivar of Geranium plant named 'Balgalsofi', characterized by its numerous single light pink-colored flowers with reddish purple central splotches and spots; floriferousness; upright, mounding and spreading growth habit; basal branching; vigor; and dark green leaves.

1 Drawing Sheet

BACKGROUND OF THE INVENTION

The present invention relates to a new and distinct cultivar of Geranium plant, botanically known as *Pelargonium peltatum×P. hortorum*, and hereinafter referred to by the cultivar name Balgalsofi.

The new Geranium is a product of a planned breeding program conducted by the Inventor in Arroyo Grande, Calif. The objective of the breeding program was to develop new cultivars with the combination of the spreading/trailing growth habit of Ivy Geraniums with the large umbels of Zonal Geraniums, freely-branching growth habit, medium green-colored foliage, uniform flowering, and interesting flower and foliage colors.

The new Geranium originated from an interspecific cross made by the Inventor of the proprietary *Pelargonium× hortorum* selection BFP-1441 as the male, or pollen parent, with the proprietary *Pelargonium peltatum* selection BFP-1114 as the female, or seed parent. The cultivar Balgalsofi was discovered and selected by the Inventor as a flowering plant within the progeny of the stated cross in a controlled environment in Arroyo Grande, Calif., in January, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balgalsofi'. There characteristics in combination distinguish 'Balgalsofi' as a new and distinct cultivar:

1. Numerous single light pink-colored flowers with reddish purple central splotches and spots; very freely flowering.
2. Upright, mounding and spreading growth habit.
3. Basal branching and vigorous.
4. Dark green leaves.

The new Geranium can be compared to the cultivar, Americana White Splash, disclosed in U.S. Plant Pat. No. 9,317. However, in side-by-side comparisons conducted in Arroyo Grande, Calif., plants of the new Geranium differ from plants of the cultivar Americana White Splash in the following characteristics:

1. Plants of the new Geranium have more leaves than plants of the cultivar Americana White Splash.
2. Plants of the new Geranium have more flowers per umbel than plants of the cultivar Americana White Splash.
3. Plants of the new Geranium have reddish purple splotches/ spots on the flower petals that are darker in color and larger than the petal spots of plants of the cultivar Americana White Splash.

A detailed comparison of plants of the cultivar Balgalsofi and the cultivar Americana White Splash, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Balgalsofi'. Flower and foliage colors in the photograph may appear different from the actual colors due to light reflectance.

DETAILED BOTANICAL DESCRIPTION

The cultivar Balgalsofi has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20 to 22° C., night temperatures about 18 to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium peltatum×P. hortorum* cultivar Balgalsofi.

Parentage:

*Male parent*.—Proprietary *Pelargonium×hortorum* selection BFP-1441.

*Female parent*.—Proprietary *Pelargonium peltatum* selection BFP-1114.

Propagation:

*Type cutting*.—Terminal cuttings.

*Time to initiate roots*.—About 7 days at 18° C.

*Time to develop roots*.—About 21 days at 18° C.

*Rooting habit*.—Fibrous and freely branching.

Plant description:

*General appearance*.—Upright, mounding and spreading growth habit. Appropriate for 10 and 12.5-cm containers.

*Crop time*.—Starting with a rooted cutting, about twelve weeks are required to produced a finished flowering plant in 10-cm container.

*Growth and branching habit*.—Vigorous and basally branching with about three or four lateral branches at the base. Pinching, that is, removal of the terminal apex, is usually not required.

*Plant height* (*to top of foliage*).—About 10 to 12 cm.

*Plant width*.—About 20 to 24 cm.

*Lateral branches*.—Length: About 5 to 7 cm. Internode length: About 2 to 2.5 cm. Color: 144C.

*Foliage description*.—Leaves simple, generally symmetrical, abundant, opposite. Quantity of leaves per lateral branch: About 11 to 13. Length: About 4.5 to 5 cm. Width: About 7.5 to 8.5 cm. Shape: Reniform. Apex: Rounded. Base: Cordate. Margin: Crenate. Venation: Palmate. Texture: Both surfaces pubescent; velvety. Color: Young foliage, upper surface: 147B. Young foliage, lower surface: 147C. Fully expanded foliage, upper surface: 147A. Fully expanded foliage, lower surface: 147B. Venation, upper surface: 144C. Venation, lower surface: 144C. Petiole: Length: About 4.5 to 7 cm. Diameter: About 2 to 3 mm. Color: 144C.

Flower description:

*Flower type and habit*.—White-colored petals with basal reddish purple spots; very floriferous. Freely and continuously fowering. Flowers arranged in substantially hemispherical umbels arising from apical leaf axils. Umbels displayed above or beyond the foliage. At full flowering, usually about four to six open umbels and two or three developing umbels per plant. Flowers single and round. Umbels persistent. Not fragrant.

*Flowering season*.—Year-round under greenhouse conditions. In the garden, flowering is continuous from spring until fall.

*Umbels*.—Number of flowers per umble: About 40 to 50. Diameter: About 11 to 13 cm. Height: About 7 to 8 cm.

*Flowers*.—Diameter: About 5 to 5.5 cm. Depth (height): About 1.3 cm.

*Flower buds*.—Length: About 1.3 to 1.7 cm. Diameter: About 6 to 9 mm. Shape: Round to oval.

*Petals*.—Quantity: About 6 petals per flower. Arrangement: Imbricate; upper two petals separate from lower petals. Length: About 2.5 to 3 cm. Width: About 2.2 to 2.4 cm. Shape: Obovate. Apex: Rounded. Base: Attenuate. Margin: Entire. Texture: Smooth; iridescent. Color, fully opened flowers: Upper surface: Background, 56D. Upper petals have venation, 61A, towards base and a large splotch of 61B distal from the venation. Lower petals have a small spot of 61C. Color fades to 161C with subsequent development. Lower surface: 155D.

*Sepals*.—Quantity: About 5, not imbricate. Length: About 1.1 to 1.3 cm. Width: About 2 to 3 mm. Shape: Lanceolate. Apex: Pointed. Margin: Entire. Texture: Pilose. Color, upper and under surfaces: 144A.

*Peduncle* (*umbel stem*).—Length: About 16 to 17 cm. Angle: Erect. Strength: Strong. Texture: Pubescent. Color: 144C.

*Pedicel* (*individual flower stem*).—Length: About 4 to 4.2 cm. Angle: Upright or outward. Strength: Moderately strong. Texture: Pubescent. Color: 144C.

*Reproductive organs*.—Androecium: Anther size: About 2 mm. Anther color: 59A. Pollen color: 32A. Gynoecium: Ovary color: Green.

Disease resistance: Resistance to pathogens common to Pelargonium has not been observed.

Seed development: Seed production has not been observed.

CHART A

| CHARCATERISTIC | 'BALGALSOFT' | 'AMERICANA WHITE SPLASH' |
|---|---|---|
| PLANT HEIGHT (to top of foliage) | About 10 to 12 cm | About 12 to 14 cm |
| PLANT WIDTH | About 20 to 24 cm | About 20 to 24 cm |
| QUANTITY OF LEAVES PER LATERAL BRANCH | About 11 to 13 | About 7 to 9 |
| LEAF TEXTURE | Velvety; pubescent | Somewhat shiny; pubescent |
| NUMBER OF FLOWERS PER UMBEL | About 40 to 50 | About 20 to 30 |
| PETAL COLOR, UPPER PETALS, UPPER SURFACE | Background, 56D; venation, 61A large splotch, 61B | Background, 155D; venation, 61A; small spot, 73A |
| PETAL COLOR, UPPER PETALS, LOWER SURFACE | 155D | 155D |
| PETAL COLOR, LOWER PETALS, UPPER SURFACE | Background, 56D; small spot, 61C | Background, 155D; small spot, 73C |
| PETAL COLOR, LOWER PETALS, LOWER SURFACE | 155D | 155D |
| POLLEN COLOR | 32A | 170A |

It is claimed:

1. A new and distinct cultivar of Geranium plant named 'Balgalsofi', as illustrated and described.

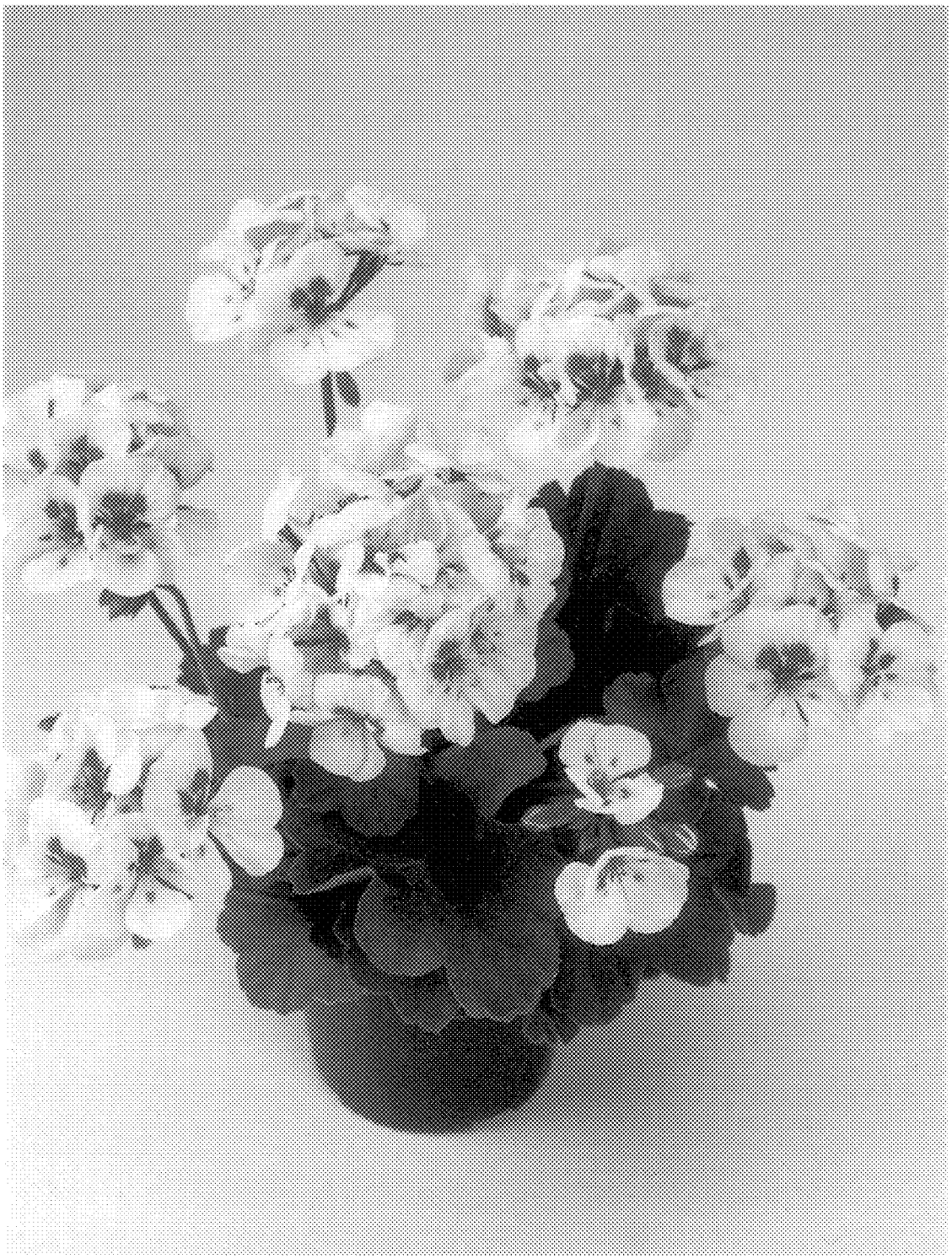

* * * * *